United States Patent [19]

Beneš et al.

[11] Patent Number: 5,112,850

[45] Date of Patent: May 12, 1992

[54] DRUG FOR TREATMENT OF GASTRIC AND DUODENAL PEPTIC ULCER DISEASE

[75] Inventors: Luděk Beneš; Viera Nosálová; Anna Babulová, all of Bratislava, Czechoslovakia

[73] Assignee: Slovenská akadémia vied, Bratislava Czechoslovakia

[21] Appl. No.: 527,189

[22] Filed: May 23, 1990

[30] Foreign Application Priority Data

May 24, 1989 [CS] Czechoslovakia ............. PV3115-89

[51] Int. Cl.$^5$ ...................... A61K 31/40; A61K 31/34
[52] U.S. Cl. ..................................... 514/428; 514/461
[58] Field of Search ........................ 514/408, 428, 461

[56] References Cited

FOREIGN PATENT DOCUMENTS 125666  1/1968  Czechoslovakia .
126102  2/1988  Czechoslovakia .

OTHER PUBLICATIONS

Babulova, A., et al., "Action of Pentacain on Gastric Acid Secretion", *Agents and Actions* (1988), vol. 23, pp. 286–288.

Toson, G. et al., "Effects of Ranitidine on Gastric Lesions and Antiinflammatory Actions of Aspirin and Indomethacin in the Rat", *Current Therapeutic Research* (1985), vol. 38, pp. 855–862.

Schotborgh, R. H., et al., "Combination Therapy of Sucralfate and Cimetidine, Compared with Sucralfate Monotherapy, in Patients with Peptic Reflux Esophagitis", *American Journal of Medicine*, 86 (Suppl 6A), 77–80, (1989).

*Ranitidine, Histamine $H_2$, Receptor Gastric Secretion in Heidenhain Pouch Dogs,* Folia pharmacol. Japon, 78, 539–547 (1981).

*New Drugs for Peptic Ulcer* by David A. Henry in *The Medical Journal of Australia*, Sep. 1, 1984, pp. 303, 304.

*Peptic Ulcer Disease, Cytoprotection and Prostaglandins* by K. Lauritsen and J. Rask-Madsen, Arch. Intern Med., vol. 150, Mar. 1990, p. 695.

Chem Abst, 108:216208v (1988). Babulova et al.
Chem Abst, 104:61855v (1986). Toson et al.

*Primary Examiner*—Frederick E. Waddell
*Assistant Examiner*—Zohreh A. Fay
*Attorney, Agent, or Firm*—Beveridge, Degrandi & Weilacher

[57] ABSTRACT

A composition for the treatment of gastric and duodenal peptic ulcer disease which is a combination of trapencaine and rantidine is disclosed.

3 Claims, No Drawings

DRUG FOR TREATMENT OF GASTRIC AND DUODENAL PEPTIC ULCER DISEASE

The invention concerns a drug acting on gastric and duodenal peptic ulcers. Its effective component is the combination of a gastroprotective and antiulcer drug with specific effect against Campylobacter pylori and of a typical representative of antisecretory drugs, belonging to $H_2$ antagonists. The efficacy of the combination is significantly greater than the effect of each drug administered separately.

The mechanism of antiulcer action is characteristic of each drug used for the treatment of gastric and duodenal peptic ulcer disease. The drugs inhibiting gastric acid secretion which are available so far, such as antagonists of histamine $H_2$ receptors e.g. cimetidine, renitidine, mifentidine (P. Del Soldato et al., Pharmacology 30, 45 (1985), Brimblecombe R. W. et al., Gastroenterology 74, 339 (1987), Daly M. et al., Br. J. Pharmacol. 72, 49 (1981) lack gastric cytoprotective effect as well as antimicrobial activity against Campylobacter pylori, a microorganism which has been reported to influence directly the development of gastric ulcers and thus to be a possible therapeutic target (Mc Nulty, J. Antimicrob. Chemother. 19, 281 (1987) ). Inhibitors of H, K-ATP ase and bismuth salts have been used in the therapy of peptic ulcer disease (A. Garner: Advances in Drug Therapy of Gastro-Intestinal Ulceration, J. Wiley et Sons Ltd., Chichester, W. Sussex, 1989) as well as anticids and prostaglandins (Ishihava K., Digestion 39, 162 (1988).

None of the above mentioned drugs possesses all types of the given antiulcer effects and after therapy withdrawal there is a high relapse rate especially when drugs such as $H_2$ antagonists are used; further problems are the cumulation of the drug in the organism (bismuth salts) and a spectrum of undesirable side effects or toxic effects (prostaglandins and others). Some of these disadvantages or shortcomings can be avoided by the combination of drugs according to the invention with the effective components /±/-trans-2-/1-pyrrolidinyl/cyklohexylester of 3-/n/pentyloxycarbanilic acid (international term trapencaine) formula I

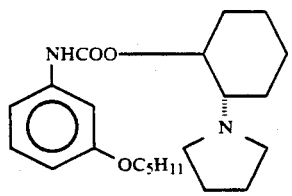

and N-/2-//5/dimethylamine/methyl/furfuryl/thio/ethyl-N'-methyl-2-nitro-1,1-ethendiamine (approved international term ranitidine) formula II

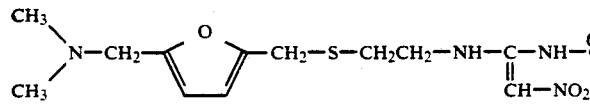

or their salts with pharmaceutically acceptable acids (weight ratio 3:10 up to 10:3) which may contain a physiologically harmless vehiculum.

The combined treatment had a profound effect both on acute gastric lesions induced by the nonsteroidal antiinflammatory drug phenylbutazone in a dose of 200 mg/kg p.o. in rats and on gastric lesions induced by restraint stress with water bath immersion, as expressed by the reduction of lesion length or by the inhibition of lesion development.

On studying the dose-response relationship of the separately administered drugs trapencaine and ranitidine, an effective inhibition of the gastric damage was observed (Tab. 1, 2).

TABLE 1

Effect of ranitidine administered orally in doses of 1, 3, 10 and 30 mg · $kg^{-1}$ on the length and number of gastric lesions induced by phenylbutazone in rats

| treatment | dose mg · $kg^{-1}$ p.o. | n | $\bar{x} \pm$ SEM | % inhibition | p |
|---|---|---|---|---|---|
| *lesion length* | | | | | |
| control ($H_2O$) | 5 ml · $kg^{-1}$ | 20 | 55.50 ± 5.64 | — | — |
| ranitidine | 1 | 10 | 43.05 ± 10.77 | 22.43 | n s |
| ranitidine | 3 | 10 | 18.80 ± 7.56 | 66.13 | 0.01 |
| ranitidine | 10 | 10 | 0.25 ± 0.17 | 99.55 | 0.01 |
| ranitidine | 30 | 10 | 0.00 ± 0.00 | 100.00 | 0.01 |
| *lesion number* | | | | | |
| control ($H_2O$) | 5 ml · $kg^{-1}$ | 20 | 22.75 ± 2.01 | — | — |
| ranitidine | 1 | 10 | 19.65 ± 3.94 | 13.63 | n s |
| ranitidine | 3 | 10 | 10.20 ± 3.58 | 55.17 | 0.01 |
| ranitidine | 10 | 10 | 0.20 ± 0.13 | 99.12 | 0.01 |
| ranitidine | 30 | 10 | 0.00 ± 0.00 | 100.00 | 0.01 | n s = nonsignificant
p versus control

On using the combination of low ineffective doses of each drug (10 mg/kg trapencaine and 3 mg/kg ranitidine) an approximately 90% inhibition of gastric damage was recorded (Tab. 3).

Individual intraduodenal administration of 10 mg/kg trapencaine or 5 mg/kg ranitidine failed to exert antisecretory effect with regard to volume of gastric juice, acidity or total acid output, whereas their combined treatment profoundly inhibited all parameters tested (Tab. 4).

TABLE 2

Effect of trapencaine administered orally in doses of 1, 3, 10 and 30 mg · $kg^{-1}$ on the length and number of gastric lesions induced by phenylbutazone in rats

| treatment | dose mg · $kg^{-1}$ p.o. | n | $\bar{x} \pm$ SEM | % inhibition | p |
|---|---|---|---|---|---|
| *lesion length* | | | | | |
| control ($H_2O$) | 5 ml · $kg^{-1}$ | 18 | 57.81 ± 6.15 | — | — |
| trapencaine | 1 | 10 | 48.65 ± 9.76 | 15.84 | n s |
| trapencaine | 3 | 8 | 37.87 ± 9.25 | 34.48 | n s |
| trapencaine | 10 | 8 | 18.69 ± 9.07 | 67.67 | 0.01 |
| trapencaine | 30 | 8 | 0.06 ± 0.06 | 99.89 | 0.01 |
| *lesion number* | | | | | |
| control ($H_2O$) | 5 ml · $kg^{-1}$ | 18 | 22.47 ± 1.84 | — | — |
| trapencaine | 1 | 10 | 20.35 ± 3.90 | 9.44 | n s |
| trapencaine | 3 | 8 | 15.81 ± 2.55 | 29.64 | n s |
| trapencaine | 10 | 8 | 6.56 ± 2.78 | 70.80 | 0.01 |
| trapencaine | 30 | 8 | 0.06 ± 0.06 | 99.72 | 0.01 |

TABLE 3

Effect of ranitidine administered in the dose of 3 mg/kg, trapencaine in the dose of 10 mg/kg and their combination on the length and number of gastric lesions induced by phenylbutazone in rats

| | treatment | dose mg · kg$^{-1}$ p.o. | n | % inhibition | p |
|---|---|---|---|---|---|
| | | | | lesion length | |
| 1/ | control (H$_2$O) | 5 ml · kg$^{-1}$ | 10 | 51.00 ± 12.09 | — | — |
| 2/ | ranitidine | 3 | 10 | 31.40 ± 9.13 | 38.43 | n s |
| 3/ | trapencaine | 10 | 10 | 17.60 ± 7.95 | 65.49 | 0.05 |
| 4/ | ranitidine + trapencaine | 3 + 10 | 10 | 4.70 ± 3.28 | 90.78 | 0.01 |
| | | | | lesion number | |
| 1/ | control (H$_2$O) | 5 ml · kg$^{-1}$ | 10 | 21.80 ± 3.80 | — | — |
| 2/ | ranitidine | 3 | 10 | 13.65 ± 3.26 | 37.39 | n s |
| 3/ | trapencaine | 10 | 10 | 7.05 ± 2.34 | 67.66 | 0.01 |
| 4/ | ranitidine + trapencaine | 3 + 10 | 10 | 2.45 ± 1.29 | 88.76 | 0.01 |

2:4 p < 0.01

TABLE 4

Effect of trapencaine in the dose of 10 mg · kg$^{-1}$ and ranitidine in the dose of 5 mg · kg$^{-1}$ and their combination administered intraduodenally on gastric acid secretion stimulated by histamine in rats

| treatment | dose mg · kg$^{-1}$ i.d. | n | volume ml · 100 g$^{-1}$ | % | acidity mmol · l$^{-1}$ | % | total acid output/umol. 100 g$^{-1}$ | % |
|---|---|---|---|---|---|---|---|---|
| control | 5 ml · kg$^{-1}$ | 11 | 4.8 ± 0.3 | — | 100.1 ± 4.6 | — | 480.9 ± 41.9 | — |
| trapencaine | 10 | 10 | 4.6 ± 0.4 | 3.6 | 93.0 ± 5.8 | 7.1 | 416.5 ± 48.5 | 13.4 |
| ranitidine | 5 | 11 | 4.3 ± 0.2 | 10.3 | 96.4 ± 1.7 | 3.7 | 413.3 ± 25.9 | 14.0 |
| trapencaine + ranitidine | 10 + 5 | 11 | 1.3 ± 0.2 | 72.5⁺ | 50.1 ± 4.9 | 50.0⁻ | 73.4 ± 14.1 | 84.7 |

TABLE 5

Effect of trapencaine in the dose of 20 mg · kg$^{-1}$, ranitidine in the dose of 10 mg · kg$^{-1}$ and their combination administered orally on gastric acid secretion stimulated by histamine in rats

| treatment | dose mg · kg$^{-1}$ p.o. | n | volume ml · 100 g$^{-1}$ | % | acidity mmol · l$^{-1}$ | % | total acid output/umol. 100 g$^{-1}$ | % |
|---|---|---|---|---|---|---|---|---|
| control | 5 ml · kg$^{-1}$ | 13 | 5.1 ± 0.2 | — | 99.9 ± 2.9 | — | 516.3 ± 29.6 | — |
| trapencaine | 20 | 14 | 4.6 ± 0.3 | 9.0 | 92.4 ± 3.7 | 7.5 | 438.5 ± 37.5 | 15.1 |
| ranitidine | 10 | 14 | 4.5 ± 0.1 | 11.9⁺ | 96.4 ± 2.4 | 3.5 | 434.2 ± 18.8 | 15.9 |
| trapencaine + ranitidine | 20 + 10 | 14 | 3.3 ± 0.2 | 36.2⁺ | 78.4 ± 3.6 | 21.5⁺ | 263.5 ± 26.5 | 49.0 | values are expressed as mean±SEM and percentage of inhibition +p versus control <0.001

Oral administration of 20 mg/kg trapencaine or of 10 mg/kg ranitidine was not effective when the drugs were administered separately, whereas the drug combination in the same doses influenced significantly gastric acid secration, expressed as percentage of inhibition (Tab. 5).

values are expressed as mean±SEM and percentage of inhibition +p versus control <0.05

On using low oral doses of separately given drugs there was a smaller inhibition of gastric secretion and again after the combined treatment a significant inhibition of volume, acidity and total acid output was achieved.

Experimentally induced chronic gastric ulcers were not significantly affected when doses of 30 mg/kg p.o. of each separately administered drug were used, while the combined treatment increased efficacy in reducing the ulcer area by 81% (Tab. 6).

Antiulcer efficacy of the combined trapencaine and ranitidine treatment is more pronounced than the effect of each drug given alone. The resulting antiulcer activity appears to be additive, in some cases synergistic. The drug according to formula I can be prepared on the basis of the Czechoslovak patents No. 125666 and No. 126102, the drug according to formula II is available from the producer.

TABLE 6

Extent of ulcer area 7 days after chronic gastric ulcer production in control (untreated) group and in the groups given ranitidine in the dose of 30 mg · kg$^{-1}$ p.o. twice daily, trapencaine in the dose of 30 mg · kg$^{-1}$ p.o. twice daily or their combination

| treatment | dose 2 × mg · kg$^{-1}$ p.o. | n | ulcer area (mm$^2$) x ± SEM | % inhibition | p |
|---|---|---|---|---|---|
| control (H$_2$O) | 5 ml · kg$^{-1}$ | 11 | 22.06 ± 4.02 | — | — |
| ranitidine | 30 | 11 | 8.98 ± 5.01 | 59.27 | n s |
| trapencaine | 30 | 11 | 15.98 ± 5.34 | 27.54 | n s |
| ranitidine + trapencaine | 30 + 30 | 10 | 4.09 ± 2.06 | 81.48 | 0.01 |

EXAMPLE

Tablet form of the antiulcer drug

Effective substances in the amount of 20 g trapencaine and 10 g ranitidine are mixed with 40 g lactose, 135 g starch and moistened with the necessary amount of starch hydrogel. The mixture is granulated, homogenised and 2 g of magnesium stearate is added.

The mixture is pressed into tablet form of approximately 250 mg, with a diameter of 5 mm. One tablet corresponds to the combined dose of 30 mg effective substances (20 mg trapencaine and 10 mg ranitidine).

We claim:

1. A drug composition for the treatment of gastric and duodenal peptic ulcer disease comprising as effective components the combination of /±/-trans-2/1-pyrrolidinyl/cyklohexylester of 3-/n/-pentyloxycarbanilic acid formula I

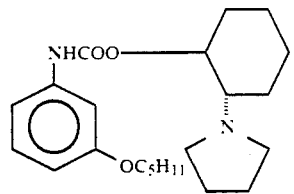

and N/2-/5-/dimethylamine/-methyl/furfuryl/thio/ethyl-N'-methyl-2-nitro-1,1-ethendiamine formula II

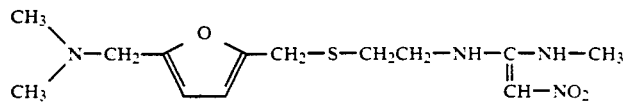

or their salts with pharmaceutically acceptable acids with the weight ratio of 3:10 up to 10:3, which may contain physiologically harmless vehicle.

2. The drug composition according to claim 1 further comprising a physiologically harmless vehicle.

3. A method of treating gastric and duodenal peptic ulcer disease comprising administering an effective amount of the drug composition of claim 1 to a patient in need thereof, wherein said drug composition is orally administered.

* * * * *